(12) United States Patent
Marinkovich et al.

(10) Patent No.: US 9,403,895 B2
(45) Date of Patent: Aug. 2, 2016

(54) PRODUCTION AND DELIVERY OF A STABLE COLLAGEN

(71) Applicants: The Board of Trustees of the Leland Stanford Junior University, Stanford, CA (US); THE UNITED STATES OF AMERICA AS REPRESENTED BY THE DEPARTMENT OF VETERANS AFFAIRS, Washington, DC (US)

(72) Inventors: M. Peter Marinkovich, Redwood City, CA (US); Alfred T. Lane, Los Altos, CA (US); Jayakumar Rajadas, Cupertino, CA (US)

(73) Assignees: The Board of Trustees of the Leland Stanford Junior University, Stanford, CA (US); The United States of America as Represented by the Department of Veterans Affairs, Washington, DC (US)

( * ) Notice: Subject to any disclaimer, the term of this patent is extended or adjusted under 35 U.S.C. 154(b) by 0 days.

(21) Appl. No.: 14/700,951

(22) Filed: Apr. 30, 2015

(65) Prior Publication Data
US 2015/0232535 A1 Aug. 20, 2015

Related U.S. Application Data

(63) Continuation of application No. 14/112,444, filed as application No. PCT/US2012/035177 on Apr. 26, 2012, now Pat. No. 9,040,484.

(60) Provisional application No. 61/479,068, filed on Apr. 26, 2011.

(51) Int. Cl.
*A61K 38/39* (2006.01)
*A61M 37/00* (2006.01)
*C07K 14/78* (2006.01)

(52) U.S. Cl.
CPC .............. *C07K 14/78* (2013.01); *A61K 38/39* (2013.01); *A61M 37/0015* (2013.01); *A61M 2037/0023* (2013.01)

(58) Field of Classification Search
None
See application file for complete search history.

(56) References Cited

U.S. PATENT DOCUMENTS

| | | | |
|---|---|---|---|
| 5,674,703 A | 10/1997 | Woo | |
| 9,040,484 B2 * | 5/2015 | Marinkovich | A61K 38/39 514/17.2 |
| 2002/0142391 A1 | 10/2002 | Kivirikko et al. | |
| 2004/0073160 A1 | 4/2004 | Pinkerton | |
| 2009/0012494 A1 | 1/2009 | Yeshurun et al. | |
| 2009/0118672 A1 | 5/2009 | Gonnelli et al. | |
| 2010/0172886 A1 | 7/2010 | Chen et al. | |
| 2013/0243822 A1 | 9/2013 | Chen et al. | |
| 2015/0011733 A1 | 1/2015 | Viswanathan et al. | |

FOREIGN PATENT DOCUMENTS

| | | |
|---|---|---|
| WO | 93/07889 A1 | 4/1993 |
| WO | 2011030148 A1 | 3/2011 |

OTHER PUBLICATIONS

Bruckner-Tuderman, "Can type VII collagen injections cure dystrophic epidermolysis bullosa?", Molecular Therapy (Jan. 2009), 17(1):6-7.
Olsen et al., "Recombinant collagen and gelatin for drug delivery", 2003, Advanced Drug Delivery Reviews, 55 (12):1547-1567.
Chen et al., The Recombinant Expression of Full-length Type VII Collagen and Characterization of Molecular Mechanisms Underlying Dystrophic Epidermolysis Bullosa, Jan. 18, 2002, vol. 277, No. 3, pp. 2118-2124, The Journal of Biological Chemistry.
Remington et al., Injection of Recombinant Human Type VII Collagen Corrects the Disease Phenotype in a Murine Model of Dystrophic Epidermolysis Bullosa, Jan. 2009, vol. 17, No. 1, pp. 26-33, Molecular Therapy.
Woodley et al., Injection of recombinant human type VII collagen restores collagen function in dystrophic epidermolysis bullosa, Jul. 2004, vol. 10, No. 7, pp. 693-695, Nature Medicine.

* cited by examiner

*Primary Examiner* — Jeffrey E Russel
(74) *Attorney, Agent, or Firm* — Pamela J. Sherwood; Bozicevic, Field & Francis LLP

(57) ABSTRACT

Improved methods are provided for the recombinant synthesis of collagen, particularly collagen VII, in host cell, and for therapeutic delivery of the same. The recombinant collagen is produced in a host cell that has increased levels of prolyl-4-hydroxylase, relative to basal cell levels. The collagen produced by the methods of the invention has increased numbers of modified proline residues, relative to a recombinant collagen produced in a host cell having basal levels of prolyl-4-hydroxylase. The increased proline modification provides for a collagen having increased stability, including increased in vivo stability.

7 Claims, 5 Drawing Sheets

Stable type VII collagen expression in CHO cell

PRODUCTION AND DELIVERY OF A STABLE COLLAGEN

FEDERALLY SPONSORED RESEARCH AND DEVELOPMENT

This invention was made with Government support under grant no. AR047223 awarded by the National Institutes of Health. The Government has certain rights in this invention.

INTRODUCTION

Collagen is one of the most important and abundant proteins in the human body, and is present in skin, cartilage, and bone. It is the major protein comprising the ECM. Collagen consists of three left-handed polyproline II-like chains supercoiled in a parallel direction with one-residue shift, resulting in a right-handed superhelix. This packing requires glycine (Gly) as the every third residue. As a result, each chain consists of a constant amino acid sequence of Gly-X-Y, where X and Y can be any amino acid residues. About 20% of the amino acids in the collagen structure are the imino acids proline and hydroxyproline. This stiff, filament shaped molecule derives its notable tensile strength from its triple helical structure and its ability to assemble into fibrous bundles. The collagen molecule is itself a rod of about 300 nm in length and 1.5 nm in diameter. The three polypeptide strands from which it is formed are wound in a left-handed helix instead of the right-handed conformation that is typical of the alpha helix. This molecule is distinctive because of the regular pattern of amino acids that are arranged to form each strand. This architecture, which places glycine with its small size in the third position, accounts for the molecules ability to form its triple helix.

Collagen has the facility of organizing into a hierarchy of aggregated structures that ultimately arrive at fibrils with diameters measuring several hundred nanometers. These fibrils display a banded structure characterized by regular 67 nm spacings. Recent atomic force microscopy has produced detailed images of these fibers that suggest the fibrils have an inhomogeneous cross-section and react mechanically as tubes instead of rods.

The uses of collagen include providing a substrate for cell growth, for example in wound dressings, and in tissue culture. For such purposes collagen can be deposited on a surface, or can be used as a three-dimensional gel. In other uses, the replacement of human tissues with human- or animal-derived tissues such as skin or bone grafts results in the improvement of the wound healing process because of the presence of collagen. The application of collagen-derived products as biomaterials has tremendous impact in biomedicine because of (i) the natural structure of these products as a biological support for cells and scaffold for tissue repair or regeneration, (ii) their biodegradability that obviates removal of implants, and (iii) their biocompatibility. Collagen has been used to design biomaterials such as wound dressings, artificial dermis, bone or tendon substitutes, tissue engineered devices, and injectable materials in plastic surgery.

For therapeutic purposes, delivery of collagen with a stable triple helix is desirable. The present invention addresses this issue.

SUMMARY OF THE INVENTION

Improved methods are provided for the recombinant synthesis of collagen, particularly collagen VII, in host cell. The collagen may be of any mammalian species, usually human or a highly similar sequence. In the methods of the invention the recombinant collagen is produced in a host cell that has increased levels of prolyl-4-hydroxylase, relative to basal cell levels. The host cell may be a mammalian cell, or may be any other suitable host cell for recombinant polypeptide production. The collagen produced by the methods of the invention has increased numbers of modified proline residues, relative to a recombinant collagen produced in a host cell having basal levels of prolyl-4-hydroxylase. The increase of modified proline residues may be 10%, 20%, 30%, 40%, 50% or more relative to recombinant collagen produced in a host cell having basal levels of prolyl-4-hydroxylase. The increased proline modification provides for a collagen having increased stability, including increased in vivo stability, e.g. an increased half-life after injection in vivo of 1.5×, 2×, 2.5×, 5×, 10× or more.

In some embodiments, delivery devices and methods of use thereof are provided for collagen and/or other therapeutic proteins. Delivery devices of interest comprise a microneedle array, usually a microneedle array of biocompatible or biodegradable polymers comprising a therapeutic protein, e.g. stable Type VII collagen, where the microneedles are of a length to penetrate the skin across the stratum corneum and into the viable epidermis. For the purposes of the present invention, it is desirable to deliver therapeutic polypeptides to the area of epidermal/dermal junction, e.g. in the treatment of acquired or genetic epidermolysis bullosa, etc.

In some embodiments of the invention a pharmaceutical formulation is provided, comprising a purified collagen produced by the methods of the invention, e.g. human collagen 7, etc., and a pharmaceutically acceptable excipient. A pharmaceutical formulation may be in the form of a dissolvable microneedle array. In other embodiments, the pharmaceutical formulation prepared by the methods of the invention is administered to an individual for therapeutic purposes relating to collagen deficiencies, particularly collagen VII deficiencies, e.g. in the treatment of acquired or genetic epidermolysis bullosa, etc. In other embodiments the collagen is administered or formulated for topical use, e.g. in wound healing.

The increased prolyl-4-hydroxylase levels in a cell producing type VII collagen may be a result of increased levels of endogenous enzyme, e.g. by the introduction of a mutation or promoter element that increases endogenous expression; or may result from introduction of an exogenous sequence encoding prolyl-4-hydroxylase operably linked to a promoter. The increased expression may be 5-fold, 10-fold, 20-fold, 50-fold or more of the level expression in the cell in the absence of genetic modification of prolyl-4hydroxylase expression. Where the prolyl-4-hydroxylase is an exogenous sequence, it may be the same or different species as the host cell and/or the collagen sequence of interest. Further, the prolyl-4-hydroxylase coding sequence may be present in the host cell on the same vector as the collagen sequence of interest, or may be present on a separate vector, or integrated into the host chromosome.

In some embodiments of the invention, a recombinant host cell is provided, wherein the host cell comprises an exogenous collagen, e.g. human collagen VII, coding sequence operably linked to a promoter sequence, which may be on an episomal vector or integrated into the host cell genome, wherein the host cell has been genetically modified to overexpress prolyl-4-hydroxylase. In some embodiments, the exogenous collagen sequence and the exogenous prolyl-4-hydroxylase are present on a single vector. In other embodiments the exogenous collagen and the exogenous prolyl-4-hydroxylase are present on different vectors. In some embodiments a recombinant expression vector is provided comprising a collagen coding sequence and a prolyl-4-hydroxylase coding sequence, each operably linked to a promoter.

DESCRIPTION OF THE SPECIFIC EMBODIMENTS

Figure 1:
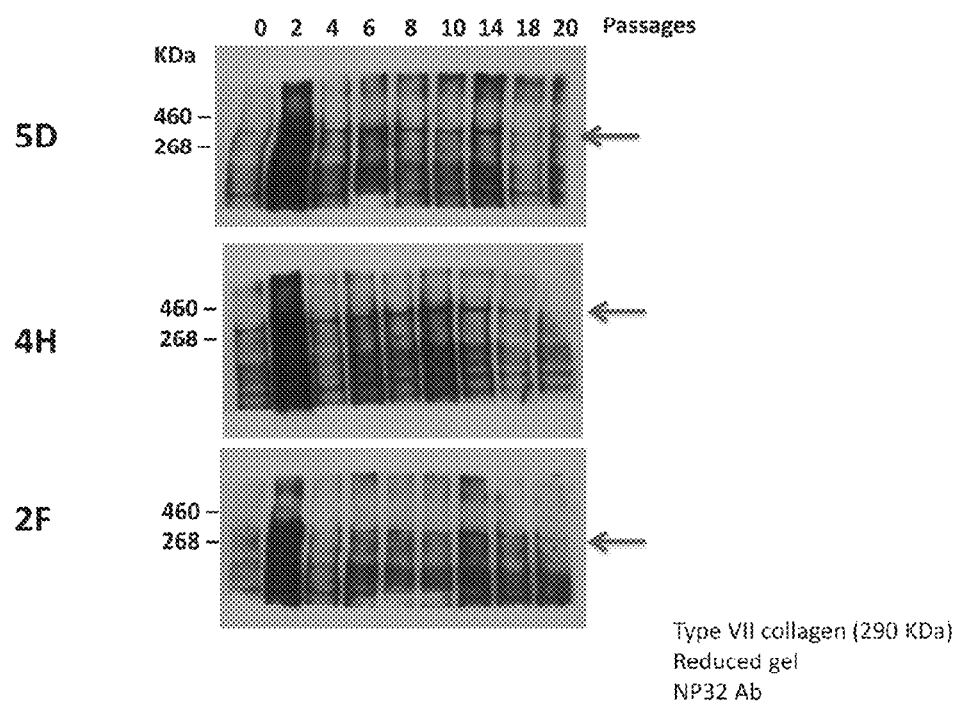
FIG. 1 shows the results of growing cloned CHO cells expressing collagen VII for up to 20 passages in the absence of selection. The type VII collagen was immunoblotted with a type VII antibody NP32, the lanes show continued stable expression of type VII collagen throughout multiple passages, which is important for a GMP manufacturing process.

It is to be understood that this invention is not limited to the particular methodology, protocols, cell lines, animal species or genera, and reagents described, as such may vary. It is also to be understood that the terminology used herein is for the purpose of describing particular embodiments only, and is not intended to limit the scope of the present invention which will be limited only by the appended claims.

As used herein the singular forms "a", "and", and "the" include plural referents unless the context clearly dictates otherwise. Thus, for example, reference to "a cell" includes a plurality of such cells and reference to "the culture" includes reference to one or more cultures and equivalents thereof known to those skilled in the art, and so forth. All technical and scientific terms used herein have the same meaning as commonly understood to one of ordinary skill in the art to which this invention belongs unless clearly indicated otherwise.

Collagen.

As used herein the term "collagen" refers to compositions in which at least about 50%, at least about 60%, at least about 70%, at least about 80%, at least about 90%, at least about 95% or more of the protein present is collagen in a triple helical configuration. The folding of the individual α-chains into the triple-helical conformation is predicated upon the characteristic primary sequence, consisting of repeating Gly-X-Y triplet sequences. Collagens are widely found in vertebrate species, and have been sequenced for many different species. Due to the high degree of sequence similarity between species, collagen from different species can be used for biomedical purposes, e.g. between mammalian species, although the human protein may be preferred FACIT collagens (fibril-associated collagens with interrupted triple helices) include types IX, XII, XIV, XIX, XX, and XXI. Several of the latter types of collagens associate with larger collagen fibers and serve as molecular bridges, stabilizing the organization of the extracellular matrix. Collagen VII, (COL7A1, Chromosome 3, NC_000003.10 (48576510 . . . 48607689, complement)) is of particular interest. Type VII collagen is a major component of anchoring fibrils.

Type VII collagen is a long, 424 nm, triple-helical domain with flanking non-collagenous sequences. Type VII collagen molecules consist of a central collagenous, triple-helical segment flanked by the non-collagenous NC-1 and NC-2 domains. Unlike interstitial collagens, the repeating Gly-X-Y sequence is interrupted by 19 imperfections due to insertions or deletions of amino acids in the Gly-X-Y repeat sequence. Most notably, in the middle of the triple-helical domain, there is a 39-amino acid non-collagenous "hinge" region which is susceptible to proteolytic digestion with pepsin. The amino-terminal NC-1 domain of type VII, approximately 145 kDa in size, consists of sub-modules with homology to known adhesive proteins, including segments with homology to cartilage matrix protein (CMP), nine consecutive fibronectin type III-like (FN-III) domains, a segment with homology to the A domain of von Willebrand factor, and a short cysteine and proline-rich region. The carboxy-terminal non-collageneous domain, NC-2, is relatively small, ~30 kDa, and it contains a segment with homology to Kunitz protease inhibitor molecule.

The human type VII collagen gene, COL7A1 has a complex structure consisting of a total of 118 separate exons. The gene is, however, relatively compact, and most of the introns are relatively small; consequently, the size of the entire human COL7A1 gene is only ~32 kb, encoding a messenger RNA of ~8.9 kb. COL7A1 has been mapped to the short-arm of human chromosome 3, region 3p21.1. The type VII collagen gene structure and the encoded primary sequence of the protein are well conserved, and for example, the mouse gene shows 84.7 percent homology at the nucleotide and 90.4 percent identity at the protein level.

Type VII collagen is synthesized both by epidermal keratinocytes and dermal fibroblasts in culture. Upon synthesis of complete pro-α1(VII) polypeptides, three polypeptides associate through their carboxy-terminal ends to a trimer molecule which in its collagenous portion folds into the triple-helical formation. The triple-helical molecules are then secreted to the extracellular milieu where two type VII collagen molecules align into an anti-parallel dimer with the amino-terminal domains present at both ends of the molecule. This dimer assembly is accompanied by proteolytic removal of a portion of the carboxy-terminal end of both type VII collagen molecules and stabilization by inter-molecular disulfide bond formation. Subsequently, a large number of these anti-parallel dimers aggregate laterally to form anchoring fibrils.

Glycine substitution mutations in the triple helical domain of COL7A (especially in exons 73, 74, and 75) predominate in dominant dystrophic epidermolysis bullosa (DDEB). Mutations p.Gly2034Arg and p.Gly2043Arg are the most common DDEB-causing mutations, making up 50% of the dominant mutations reported in the largest US cohort. Glycine substitutions as well as other amino acid substitutions and splice junction mutations outside of this region may also be found in dominant DEB.

More than 400 recessive DEB-causing mutations spanning the entire gene have been described for all forms of DEB. Each mutation, however, accounts for no more than 1%-2% of the total number of mutations described. Null mutations predominate in RDEB, though glycine substitutions and other amino acid substitutions have been described. Milder forms of RDEB are often caused by splice junction mutations or other missense mutations.

According to the methods of the invention, composition are provided of a recombinantly produced Type VII collagen, which has been post-translationally modified by recombinantly expressed prolyl 4 hydroxylase, thereby increasing the stability of the collagen composition relative to the unmodified form.

A "native sequence" polypeptide is one that has the same amino acid sequence as a polypeptide derived from nature. Such native sequence polypeptides can produced by recombinant means according to the methods set forth herein. Thus, a native sequence polypeptide can have the amino acid sequence of, e.g. naturally occurring human polypeptide, murine polypeptide, or polypeptide from any other mammalian species, and the like. The term "native sequence collagen VII protein" includes the native proteins with or without the initiating N-terminal methionine (Met).

A "variant" polypeptide means a biologically active polypeptide as defined below having less than 100% sequence identity with a native sequence polypeptide. Such variants include polypeptides wherein one or more amino acid residues are added at the N- or C-terminus of, or within, the native sequence; from about one to forty amino acid residues are deleted, and optionally substituted by one or more amino acid residues; and derivatives of the above polypeptides, wherein an amino acid residue has been covalently modified so that the resulting product has a non-naturally occurring amino acid. Ordinarily, a biologically active collagen VII variant will have an amino acid sequence having at least about 90% amino acid sequence identity with a native sequence collagen VII polypeptide, preferably at least about 95%, more preferably at least about 99%.

A "functional derivative" of a native sequence collagen VII polypeptide is a compound having a qualitative biological property in common with a native sequence collagen VII polypeptide. "Functional derivatives" include, but are not limited to, fragments of a native sequence and derivatives of a native sequence collagen VII polypeptide and its fragments, provided that they have a biological activity in common with a corresponding native sequence collagen VII polypeptide. The term "derivative" encompasses both amino acid sequence variants of collagen VII polypeptide and covalent modifications thereof.

Prolyl 4-hydroxylase (EC 1.14.11.2) plays a central role in collagen synthesis. It catalyzes the formation of 4-hydroxyproline in collagens by hydroxylation of proline residues in peptide linkages. The 4-hydroxyproline residues are essential for the folding of the newly synthesized procollagen polypeptide chain into triple helical molecules. The active enzyme is a tetramer of 2 alpha and 2 beta subunits with a molecular weight of about 240,000. The beta subunit (P4HB) is identical to the enzyme disulfide isomerase (EC 5.3.4.1) and a major cellular thyroid-binding protein. The alpha subunit contributes a major part of the catalytic site of the enzyme. The polypeptide is 517 amino acid residues and a signal peptide of 17 amino acids.

The P4HA gene covers more than 69 kilobases and consists of 16 exons. Evidence had previously been presented for a mutually exclusive alternative splicing of RNA transcripts of the gene. The present data indicated that the mutually exclusive sequences found in the mRNAs are coded by 2 consecutive, homologous 71-bp exons, 9 and 10. These exons are identical in their first 5 base pairs and the overall identity between them is 61% at the nucleotide level and 58% at the level of the coded amino acids. Both types of mRNA were found to be expressed in all of the tissues studied, but in some tissues the type coding for the exon 9 or exon 10 sequences was more abundant than the other type.

Expression Construct:

In the present methods, collagen VII is produced by recombinant methods. The DNA encoding collagen VII polypeptide may be obtained from any cDNA library prepared from tissue expressing the collagen VII polypeptide mRNA, prepared from various sources. The Collagen VII polypeptide-encoding gene may also be obtained from a genomic library or by oligonucleotide synthesis. An alternative means to isolate the gene encoding is to use PCR methodology.

The nucleic acid (e.g., cDNA or genomic DNA) encoding the collagen VII polypeptide is inserted into a replicable vector for expression, operably linked to elements required for expression. Many such vectors are available. The vector components generally include, but are not limited to, one or more of the following: an origin of replication, one or more marker genes, an enhancer element, a promoter, and a transcription termination sequence. The vector may further comprise a prolyl 4 hydroxylase operably linked to elements required for expression. Alternatively, the prolyl 4 hydroxylase is provided on a second expression vector.

Nucleic acids are "operably linked" when placed into a functional relationship with another nucleic acid sequence. For example, DNA for a signal sequence is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adapters or linkers are used in accordance with conventional practice.

Expression vectors usually contain a selection gene, also termed a selectable marker. This gene encodes a protein necessary for the survival or growth of transformed host cells grown in a selective culture medium. Host cells not transformed with the vector containing the selection gene will not survive in the culture medium. Typical selection genes encode proteins that (a) confer resistance to antibiotics or other toxins, e.g., ampicillin, neomycin, methotrexate, or tetracycline, (b) complement auxotrophic deficiencies, or (c) supply critical nutrients not available from complex media.

Expression vectors will contain a promoter that is recognized by the host organism and is operably linked to the collagen VII coding sequence. Promoters are untranslated sequences located upstream (5') to the start codon of a structural gene (generally within about 100 to 1000 bp) that control the transcription and translation of particular nucleic acid sequence to which they are operably linked. Such promoters typically fall into two classes, inducible and constitutive. Inducible promoters are promoters that initiate increased levels of transcription from DNA under their control in response to some change in culture conditions, e.g., the presence or absence of a nutrient or a change in temperature. A large number of promoters recognized by a variety of potential host cells are well known. Heterologous promoters are preferred, as they generally permit greater transcription and higher yields.

Transcription from vectors in mammalian host cells may be controlled, for example, by promoters obtained from the genomes of viruses such as polyoma virus, fowlpox virus, adenovirus (such as adenovirus 2), bovine papilloma virus, avian sarcoma virus, cytomegalovirus, a retrovirus, hepatitis-B, simian virus 40 (SV40), from heterologous mammalian promoters, e.g., the actin promoter, PGK (phosphoglycerate kinase), or an immunoglobulin promoter, from heat-shock promoters, provided such promoters are compatible with the host cell systems. The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment.

Transcription by higher eukaryotes is often increased by inserting an enhancer sequence into the vector. Enhancers are cis-acting elements of DNA, usually about from 10 to 300 bp, which act on a promoter to increase its transcription. Enhancers are relatively orientation and position independent, having been found 5' and 3' to the transcription unit, within an intron, as well as within the coding sequence itself. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin, the cytomegalovirus early promoter enhancer, the polyoma enhancer on the late side of the replication origin, and adenovirus enhancers. The enhancer may be spliced into the expression vector at a position 5' or 3' to the coding sequence, but is preferably located at a site 5' from the promoter.

Expression vectors used in eukaryotic host cells will also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA.

Particularly useful in the practice of this invention are expression vectors that provide for the transient expression in mammalian cells. In general, transient expression involves the use of an expression vector that is able to replicate efficiently in a host cell, such that the host cell accumulates many copies of the expression vector and, in turn, synthesizes high levels of a desired polypeptide encoded by the expression vector. Transient expression systems, comprising a suitable expression vector and a host cell, allow for the convenient positive identification of polypeptides encoded by cloned DNAs, as well as for the rapid screening of such polypeptides for desired biological or physiological properties.

In a preferred embodiment, the proteins are produced in vertebrate cells, and more particularly in vertebrate cells that, upon expression of a collagen VII protein, post-translationally modify the protein as a result of over-expression of prolyl 4 hydroxylase.

Examples of useful mammalian host cell lines include, without limitation, mouse L cells (L-M[TK-], ATCC#CRL-2648), monkey kidney CV1 line transformed by SV40 (COS-7, ATCC CRL 1651); human embryonic kidney line (293 or 293 cells subcloned for growth in suspension culture; baby hamster kidney cells (BHK, ATCC CCL 10); Chinese hamster ovary cells/-DHFR (CHO); mouse sertoli cells (TM4); monkey kidney cells (CV1 ATCC CCL 70); African green monkey kidney cells (VERO-76, ATCC CRL-1 587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells; MRC 5 cells; FS4 cells; and human hepatoma line (Hep G2).

Host cells are transfected with the above-described expression vectors for collagen VII and prolyl 4 hydroxylase polypeptide production, and cultured in conventional nutrient media modified as appropriate for inducing promoters, selecting transformants, or amplifying the genes encoding the desired sequences. Mammalian host cells may be cultured in a variety of media. Commercially available media such as Ham's F10 (Sigma), Minimal Essential Medium ((MEM), Sigma), RPMI 1640 (Sigma), and Dulbecco's Modified Eagle's Medium ((DMEM), Sigma) are suitable for culturing the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleosides (such as adenosine and thymidine), antibiotics, trace elements, and glucose or an equivalent energy source. Any other necessary supplements may also be included at appropriate concentrations that would be known to those skilled in the art. The culture conditions, such as temperature, pH and the like, are those previously used with the host cell selected for expression, and will be apparent to the ordinarily skilled artisan.

Microneedles (MN), as used herein, refers to an array comprising a plurality of micro-projections, generally ranging from about 25 to about 2000 μm in length, which are attached to a base support. An array may comprise $10^2$, $10^3$, $10^4$, $10^5$ or more microneedles, and may range in area from about 0.1 cm$^2$ to about 100 cm$^2$. Application of MN arrays to biological membranes creates transport pathways of micron dimensions, which readily permit transport of macromolecules such as large polypeptides. In some embodiments of the invention, the microneedle array is formulated as a transdermal drug delivery patch. MN arrays can alternatively be integrated within an applicator device which, upon activation, can deliver the MN array into the skin surface, or the MN arrays can be applied to the skin and the device then activated to push the MN through the SC.

Various materials have been used for microneedles. For the purposes of the present invention, biodegradable materials into which the therapeutic protein can be incorporated are of particular interest. Such materials include various biodegradable or biocompatible polymers or cross-linked monomers, as known in the art. The dose of protein to be delivered will vary, and may range from at least about 1 ng/microneedle array, at least about 10 ng, at least about 0.1 μg, at least about 1 μg, at least about 10 μg or more in a single array. MNs may be fabricated with a wide range of designs (different sizes and shapes) and different types (solid, hollow, sharp, or flat), and may be in-plane and/or out-of-plane.

Polymeric MNs can provide biocompatibility, biodegradability, strength, toughness, and optical clarity. To accurately produce the micro-scale dimensions of polymer MNs, a variety of mould-based techniques, such as casting, hot embossing, injection molding, and investment molding may be used, e.g. beveled-tip, chisel-tip, and tapered-cone polydimethylsiloxane (PDMS) molds. Polymeric materials of interest for fabrication include without limitation; poly (methylmethacrylate) (PMMA), poly-L-lactic acid (PLA), poly-glycolic acid (PGA), and poly-lactic-co-glycolic acid (PLGA), cyclic-olefin copolymer, poly (vinyl pyrrolidone), and sodium carboxymethyl cellulose. Sugars have also been used to fabricate the MNs, such as galactose, maltose, aliginate, chitosan, and dextrin. Materials may be cross-linked through ion exchange, photo-polymerization, and the like.

Conditions of interest for treatment with a recombinantly prepared collagen formulation of the present invention include, without limitation, various forms of epidermolysis bullosa, including acquired and congenital forms, the latter of which may be recessive or dominant.

Based on the most recent classification system, dystrophic epidermolysis bullosa (DEB) includes three subtypes: recessive DEB, severe generalized (RDEB-sev gen) (formerly called Hallopeau-Siemens type (RDEB-HS); recessive DEB, generalized other (RDEB-O) (formerly called non-Hallopeau-Siemens type (RDEB-non-HS); and dominant DEB (DDEB). In RDEB-sev gen, blisters affecting the whole body may be present in the neonatal period. Oral involvement may lead to mouth blistering, fusion of the tongue to the floor of the mouth, and progressive diminution of the size of the oral cavity. Esophageal erosions can lead to webs and strictures that can cause severe dysphagia. Consequently, severe nutritional deficiency and secondary problems are common. Corneal erosions can lead to scarring and loss of vision. Blistering of the hands and feet followed by scarring fuses the digits into "mitten" hands and feet, a hallmark of this disorder. The lifetime risk of aggressive squamous cell carcinoma is over 90%. In DDEB, blistering is often mild and limited to hands, feet, knees, and elbows, but nonetheless heals with scarring. Dystrophic nails, especially toenails, are common and may be the only manifestation of DDEB.

Conventional treatment of manifestations is primarily supportive, including wound dressing and nutritional support. Occupational therapy may help prevent hand contractures. Surgical release of fingers often needs to be repeated.

Type VII collagen find use as a protein therapy for dystrophic epidermolysis bullosa, see for example, Remington et al. (2009) Mol Ther. 17(1):26-33, herein specifically incorporated by reference. This type of therapy require repeated injections, e.g. intradermal injections, the frequency of which would depend on the in vivo stability of the recombinant collagen molecule.

In addition to inherited forms of EB, the acquired form of epidermolysis bullosa (EBA) involves pathology in type VII collagen and may be treated with the compositions of the method. Specifically, circulating autoantibodies in patients with EBA recognize epitopes in type VII collagen molecules, and molecular cloning of the type VII collagen cDNAs again provided the tools to identify the most predominant immunoepitopes within the amino-terminal NC-1 domain of type VII collagen. The antigenic properties of the NC-1(VII) domain are further highlighted by the fact that monoclonal antibodies, such as H3A and L3D, which are in clinical use to map type VII collagen in the skin of patients with inherited forms of EB, also identify epitopes in this portion of the protein. In addition to circulating autoantibodies recognizing type VII collagen epitopes in EBA, bullous lesions in some patients with systemic lupus erythematosus have also been associated with anti-type VII collagen antibodies.

Purification and Formulation of Collagen VII Protein

Collagen VII proteins produced by the methods of the invention are preferably recovered from the culture medium as a secreted polypeptide, although it can also be recovered from host cell lysates. The final collagen VII composition may be affinity purified, chromatographically separated, concentrated, filtered, dialyzed, etc., using methods known in the art. For therapeutic applications, the Collagen VII polypeptides are administered to a mammal, preferably a human, in a physiologically acceptable dosage form, including those that may be administered to a human intradermally as a bolus or by continuous infusion over a period of time. Alternative routes of administration include intramuscular, intraperitoneal, subcutaneous, intra-articular, intrasynovial, or topical routes.

Such dosage forms encompass physiologically acceptable carriers that are inherently non-toxic and non-therapeutic. Examples of such carriers include ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts, or electrolytes such as protamine sulfate, disodium hydrogen phosphate, potassium hydrogen phosphate, sodium chloride, zinc salts, colloidal silica, magnesium trisilicate, polyvinyl pyrrolidone, cellulose-based substances, and PEG.

Carriers for topical or gel-based forms of Collagen VII polypeptides, including wound dressings, include polysaccharides such as sodium carboxymethylcellulose or methylcellulose, polyvinylpyrrolidone, polyacrylates, polyoxyethylene-polyoxypropylene-block polymers, PEG, and wood wax alcohols. For all administrations, conventional depot forms are suitably used. Such forms include, for example, microcapsules, nano-capsules, liposomes, plasters and sustained-release preparations. The collagen VII polypeptide will typically be formulated in such vehicles at a concentration of about 0.1 µg/ml to 100 µg/ml.

In some embodiments of the invention a patient is treated by dermal injection of Collagen VII produced by the methods of the invention. The injection may be performed by fabricating a microneedle array comprising therapeutic proteins of the invention, and contacting the patient skin with the microneedle array at a pressure or with a device suitable to deliver the microneedles to the dermal layer. In some embodiments the microneedles are biodegradable, and are left in situ to deliver the protein over time. The area to be treated, and the timing and dose of delivery are determined based on the needs of the individual patient, the condition, the composition of the microneedle array, and the like.

In another embodiment of the invention, an article of manufacture containing materials useful for the treatment of the conditions described above is provided. Such an article of manufacture may include a microneedle array, as described herein. The microneedle array may be loaded with an effective dose of therapeutic proteins of the invention.

Alternatively the article of manufacture may comprise a container and a label. Suitable containers include, for example, bottles, vials, syringes, and test tubes. The containers may be formed from a variety of materials such as glass or plastic. The container holds a composition that is effective for treating the condition and may have a sterile access port (for example the container may be an intravenous solution bag or a vial having a stopper pierceable by a hypodermic injection needle). The active agent in the composition is the collagen VII protein. The label on, or associated with, the container indicates that the composition is used for treating the condition of choice. Further container(s) may be provided with the article of manufacture which may hold, for example, a pharmaceutically-acceptable buffer, such as phosphate-buffered saline, Ringer's solution or dextrose solution. The article of manufacture may further include other materials desirable from a commercial and user standpoint, including other buffers, diluents, filters, needles, syringes, and package inserts with instructions for use.

EXPERIMENTAL

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

All publications and patent applications cited in this specification are herein incorporated by reference as if each individual publication or patent application were specifically and individually indicated to be incorporated by reference.

The present invention has been described in terms of particular embodiments found or proposed by the present inventor to comprise preferred modes for the practice of the invention. It will be appreciated by those of skill in the art that, in light of the present disclosure, numerous modifications and changes can be made in the particular embodiments exemplified without departing from the intended scope of the invention. For example, due to codon redundancy, changes can be made in the underlying DNA sequence without affecting the protein sequence. Moreover, due to biological functional equivalency considerations, changes can be made in protein structure without affecting the biological action in kind or amount. All such modifications are intended to be included within the scope of the appended claims.

Example 1

Figure 2:
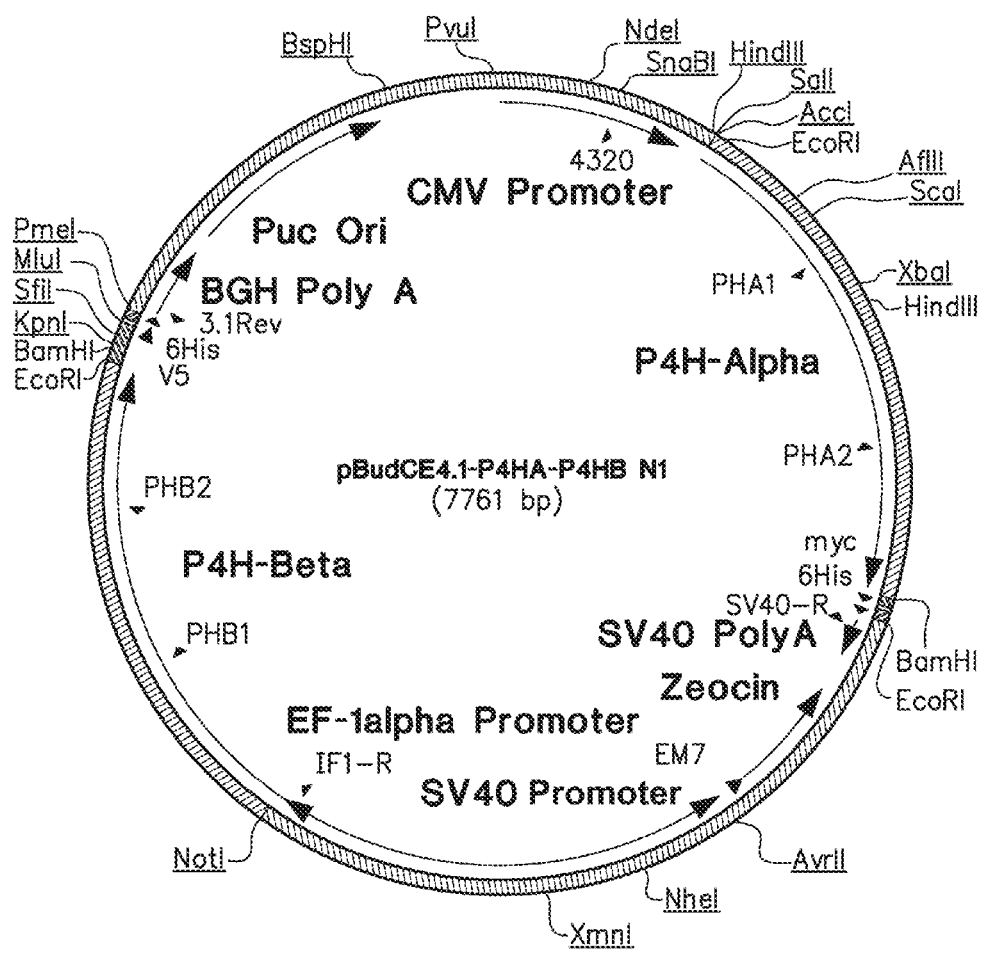
FIG. 2 is a diagram of a vector for transfection of a gene encoding prolyl hydroxylase, the enzyme which stabilizes the collagen. It is a two subunit protein; each subunit is expressed from a single plasmid. It has a zeocin resistance gene for selection purposes. Cells were transfected by electroporation, $10^7$ cells with 40 mg of linearized plasmid, exponential decay −300V/90 mF/resistance.
Figure 3:
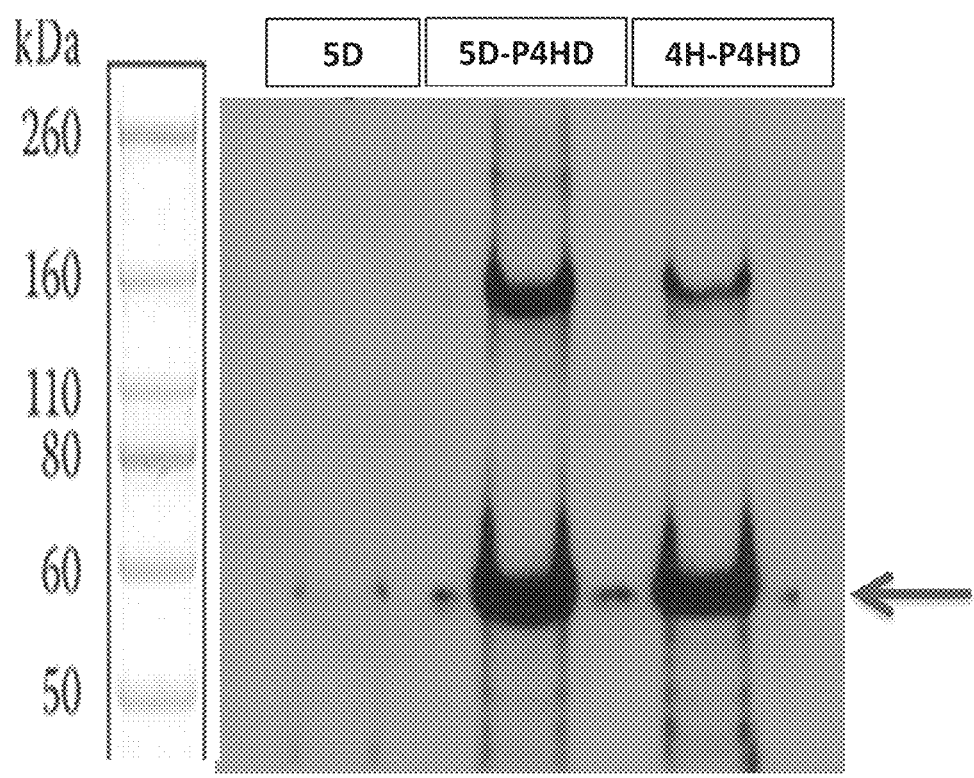
FIG. 3 is a western blot showing expression of individual clones of stable type VII collagen expressing 293 clones expressing prolyl hydroxylase protein. The type VII collagen on the reduced media lane shows the molecular weight of around 290 kDa which is full length type VII collagen, however the media from the non-reduced sample is also the same molecular weight. This shows that the collagen is migrating as a monomer, even though its native state is a trimer—the collagen triple helix is not stable enough to withstand the conditions of SDS electrophoresis, but rather it breaks apart into a monomer under these conditions.
Figure 4:
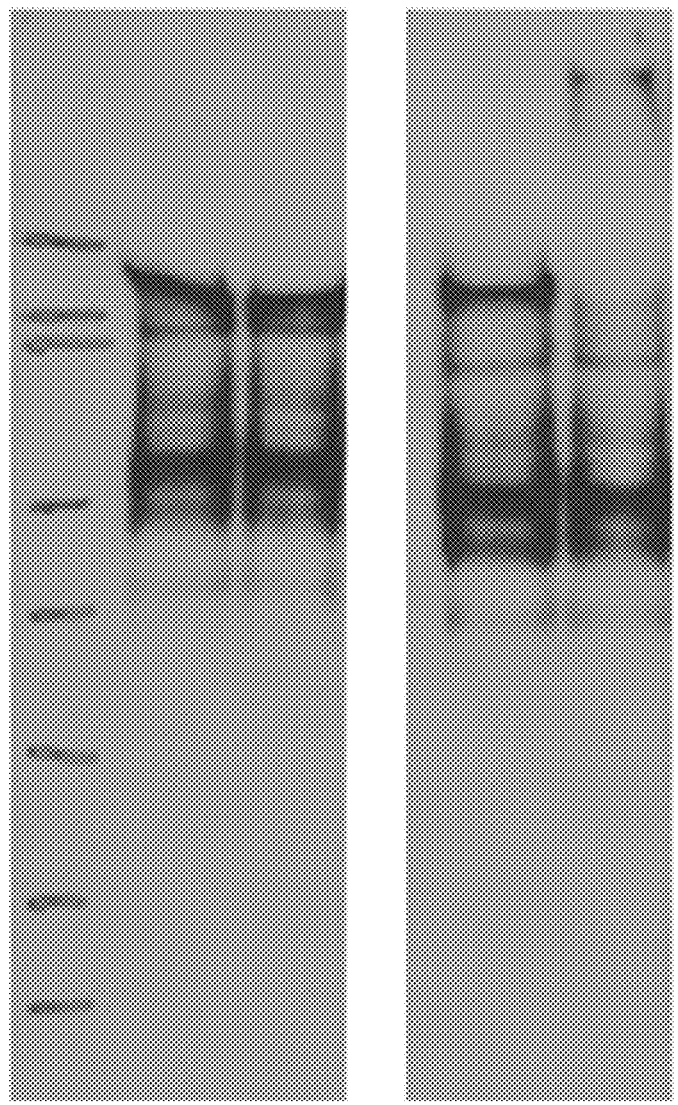
FIG. 4 shows medium from 293 cells, which are overexpressing both collagen VII and prolyl hydroxylase. This gel shows that, while under reducing conditions the collagen migrates as a monomer, but under non reducing conditions the collagen migrates clearly as a trimer. This indicates a greater degree of triple helical stability, which is provided by the added prolyl hydroxylation of this protein by the co expressed prolyl hydroxylase, so that it can remain a trimer during non-reducing SDS electrophoresis. The data indicate that increased prolyl hydroxylation of type VII collagen produces a more stable trimer.
Figure 5:
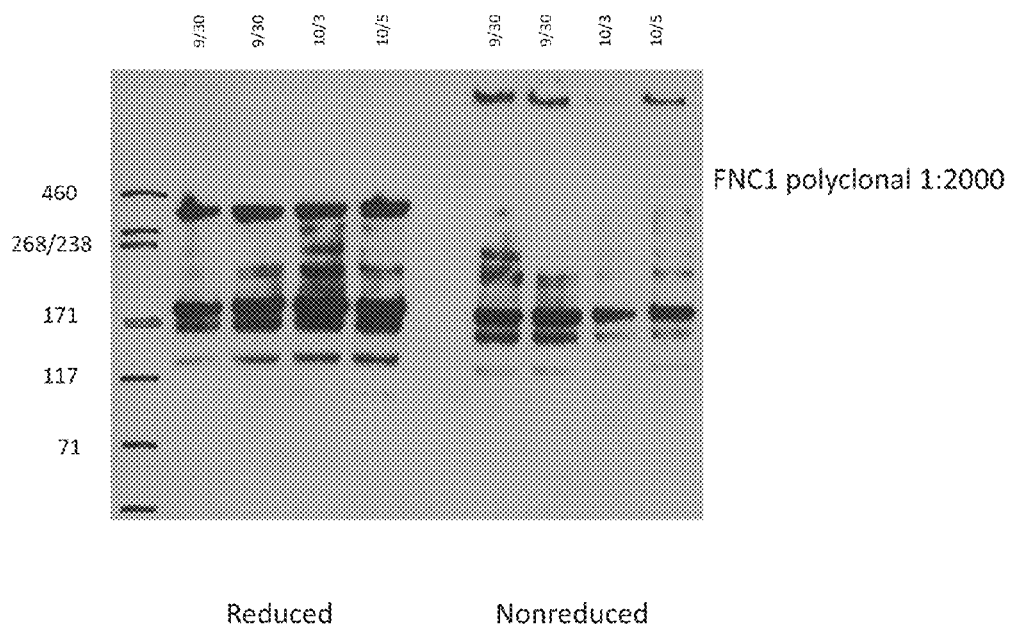
FIG. 5 is a western blot showing expression of individual clones of stable type VII collagen expressing cells under reducing and non-reducing conditions.

Expression of Type VII Collagen in the Presence of High Levels of Prolyl Hydroxylase As shown in FIG. 1, cloned CHO cells express collagen VII for up to 20 passages in the absence of selection. Using a vector shown in FIG. 2, cells were electroporated to over-express the two subunits of prolyl hydroxylase. As shown in FIG. 3, cells expressing type VII collagen with normal levels of prolyl hydroxylase expression express a weakly trimeric form of the collagen. In contrast, as shown in FIG. 4, cells that over-express both collagen VII and prolyl hydroxylase produce a type VII collagen that produces a stable trimer under non reducing SDS gel conditions. The data indicate that increased prolyl hydroxylation of type VII collagen produces a more stable trimer.

Example 2

Microneedle Patch Delivery of Type VII Collagen to the Skin

Dystrophic epidermolysis bullosa (DEB) is a severe genetic blistering disease characterized by a lack of functional type VII collagen (C7) in the dermal-epidermal basement membrane. C7 forms into a structural anchoring fibrils which bind the outer layer of the skin, called the epidermis, to the inner layer of the skin, called the dermis. Patients with defective production of C7 develop DEB.

Protein therapy, consisting of injections of purified recombinant C7, has been verified as a useful therapy in animal models, but a more effective and efficient delivery method is desirable.

Microneedle technology is provided to deliver C7 to the area of epidermal dermal junction where it can be incorporated and form anchoring fibrils. Microneedles are micron-scale structures that painlessly pierce into the skin to inject proteins or other materials. The microneedles are placed at the depth of anchoring fibrils in the skin so that the C7 can form new viable anchoring fibrils as the C7 is released into the skin. The microneedles dissolve and deliver the C7 to the specific area of the skin where anchoring fibrils form.

Protocol for fabrication of alginate needle array film: make plaster of paris (POP) mold with 50% 50% pop and 50% water, and allow to set at room temperature. Just prior to complete solidification of mold, place glass micro pillar patch on mold and compress using weight, allowing needle void array formation on mold. Make 0.5% (w/v) sodium alginate solution by dissolving sodium alginate in water with Collagen VII 0.1% (w/v), preferably produced by the methods of the invention. Pour the sodium alginate solution over the glass micro pillars impression mold and allow to fill to sit for 30 minutes in a vacuum desicator. Pour the same volume of 30 mM calcium chloride solution over the area where the alginate solution was poured.

The calcium ions cleave off the sodium ions in the alginate, and the bivalent calcium ion inserts itself into the -G-M- structure of the alginate. Since the calcium ion is bivalent, it cross links the alginate and compress into an egg-box structure, therefore forming a gel. The alginate while still in solution form fills in the needle voids made into the mold, the delayed gelation occurs even in the voids, leaving a needle array film. A vacuum can be applied to pull the alginate into the micropores more fully. The excess water is poured off, and the film peeled off and dried.

A protocol for a chitosan needle array is similar, except that phosphate is used as the cross-linker. 0.5 g of (w/v) chitosan is dissolved in 100 ml 2% (w/w) acetic acid solution under vigorous stirring for about 3 h at room temperature. The viscous solution of chitosan with Collagen VII is layered on the glass pillar mold made with plaster of paris. After 15 minutes of dessication, sodium hexameta polyphosphate SHMP (4%, w/w) solution at pH 5.4 is poured onto the chitosan layer for cross linking. The degree of cross-linking in micro needles is controlled by taking SHMP at different concentrations.

The microneedles are used to insert C7 into the skin basement membrane in patients who cannot make C7. Incorporation of C7 into the microneedles is a novel method of delivery of C7 to the large surface areas necessary to treat patients with a genetic defect involving all of their skin. This makes protein delivery into the affected skin much more easily done with less discomfort and greater accuracy than needle and syringe injections. The needles may also allow repair of current wounds by application at the junction of the wound and non-wounded skin.

There are other forms of epidermolysis bullosa (EB) missing proteins other than C7. The microneedle method of the invention can be adapted to deliver various proteins, providing a new way to deliver therapeutic proteins to patients with these diseases.

What is claimed is:

1. A method of delivering collagen VII to the dermal layer of skin, the method comprising:

fabricating an array of biodegradable microneedles comprising collagen VII incorporated into the microneedles; and contacting the skin of an individual with said array with a pressure sufficient to penetrate the skin to the depth of anchoring fibrils.

2. The method of claim 1, wherein the method further comprises:

producing collagen VII for incorporation into the microneedles, by synthesizing recombinant collagen VII in a host cell that has been genetically modified to increase expression of prolyl-4-hydroxylase.

3. The method of claim 2, wherein said individual suffers from epidermolysis bullosa.

4. An array of biodegradable microneedles, wherein said microneedles comprise collagen VII incorporated into the microneedles.

5. The array of claim 4, wherein said collagen VII is produced by the method of synthesizing recombinant collagen VII in a host cell that has been genetically modified to increase expression of prolyl-4-hydroxylase;

wherein recombinantly produced collagen VII has increased stability relative to a collagen produced in a comparable host cell lacking said genetic modification.

6. The method of claim 1, wherein the microneedles are comprised of alginate or chitosan mixed with Collagen VII.

7. The array of claim 4, wherein the microneedles are comprised of alginate or chitosan mixed with Collagen VII.

* * * * *